United States Patent [19]

Spatz et al.

[11] 4,308,213

[45] Dec. 29, 1981

[54] META-(PHENYLALKOXY)PHENYL-N-METHOXY-N-METHYLUREA COMPOUNDS

[75] Inventors: David M. Spatz, Trenton; Barrington Cross, Rocky Hill, both of N.J.

[73] Assignee: American Cyanamid Company, Stamford, Conn.

[21] Appl. No.: 152,879

[22] Filed: May 23, 1980

Related U.S. Application Data

[63] Continuation of Ser. No. 30,676, Apr. 16, 1979, Pat. No. 4,221,817.

[51] Int. Cl.$^3$ .................. C07D 317/12; C07C 83/10
[52] U.S. Cl. .................. 260/453 RW; 260/340.9 R
[58] Field of Search ............. 260/453 RW, 340.9 R

[56] References Cited

U.S. PATENT DOCUMENTS 3,642,891 2/1972 Teach .................. 260/453 RW

FOREIGN PATENT DOCUMENTS 767535 5/1971 Belgium .................. 260/453 RW

*Primary Examiner*—John M. Ford
*Assistant Examiner*—Robert C. Whittenbaugh
*Attorney, Agent, or Firm*—William H. Calnan, IV

[57] ABSTRACT

There are provided certain substituted phenylalkoxyphenylurea compounds, methods for the preparation thereof, and methods for the selective control of dicotyledonous and certain monocotyledonous plants in the presence of agronomic crops.

8 Claims, No Drawings

META-(PHENYLALKOXY)PHENYL-N-METHOXY-N-METHYLUREA COMPOUNDS

This is a continuation of application Ser. No. 30,676, filed Apr. 16, 1979 now U.S. Pat. No. 4,221,817.

SUMMARY OF THE INVENTION

The present invention relates to herbicidal urea compounds of formula (I):

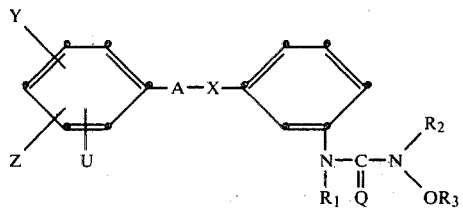

wherein X is selected from O, S, SO and $SO_2$; Q is O or S; Y is selected from the group consisting of hydrogen, halogen, $C_1$-$C_4$ alkyl, $C_2$-$C_5$ alkenyl, $C_2$-$C_5$ alkynyl, $C_1$-$C_4$ alkoxy, $CH_3S$, $CH_3SO_2$, $CF_3$, CN, $NO_2$, $NH_2$, $C_1$-$C_3$ alkylamino,

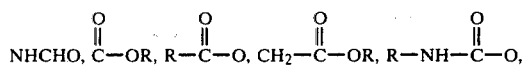

OH, $OSO_2CH_3$, $OCF_2H$, $OCF_3$ and $OCF_2Cl$; Z is selected from the group consisting of hydrogen, $C_1$-$C_4$ alkyl, $C_1$-$C_4$ alkoxy, halogen, $CF_3$ and $NO_2$; U is hydrogen, $C_1$-$C_3$ alkyl, $C_1$-$C_3$ alkoxy and halogen; A represents a $C_2$-$C_6$ carbon chain which may be saturated or unsaturated, and is optionally monosubstituted with $C_1$-$C_3$ alkyl, $C_1$-$C_3$ alkoxy, phenyl, $CF_3$, $CH_3S$, CN, halogen,

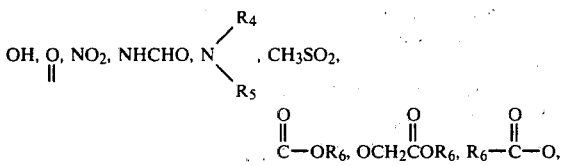

or is optionally disubstituted wherein one of the substituents is selected from the hereinabove-named group and the second substituent is selected from $C_1$-$C_3$ alkyl or halogen; or A is a moiety represented by formula:

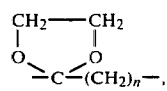

wherein n is an integer from 1 to 5; R is $C_1$-$C_4$ alkyl; $R_1$ is selected from hydrogen, $CH_3$ and CHO; $R_2$ is selected from hydrogen, $C_1$-$C_2$ alkyl, $C_3$ alkenyl or $C_3$ alkynyl; $R_3$ is selected from $C_1$-$C_3$ alkyl, $C_3$ alkenyl or $C_3$ alkynyl, with the proviso that one of $R_1$ and $R_2$ must be hydrogen or CHO; $R_4$ and $R_5$ each are hydrogen or $C_1$-$C_3$ alkyl; $R_6$ is $C_1$-$C_3$ alkyl.

A preferred group of compounds of formula (I) are those wherein X is O; Q is O; Y and Z each are selected from hydrogen, Cl, F, $C_1$-$C_4$ alkyl, $C_1$-$C_4$ alkoxy, $NO_2$; U is hydrogen; A is saturated $C_2$-$C_4$ carbon chain optionally monosubstituted with $C_1$-$C_2$ alkyl, $CH_3O$, $CH_3S$, $CH_3O_2S$, CN, Br, Cl, F,

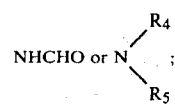

$R_1$ is hydrogen or CHO; $R_2$ and $R_3$ each are $C_1$-$C_2$ alkyl; $R_4$ and $R_5$ each are hydrogen or $C_1$-$C_3$ alkyl.

A more preferred group of compounds of formula (I) is represented by formula (Ia) below:

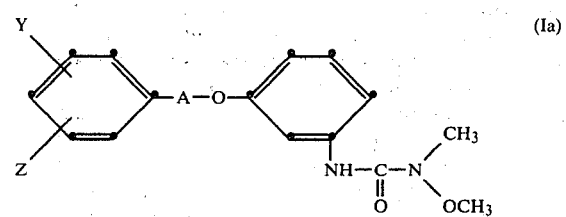

wherein Y is selected from hydrogen, $CH_3$ and Cl; Z is selected from hydrogen, $CH_3$, $CH_3O$, Cl and F; A is selected from

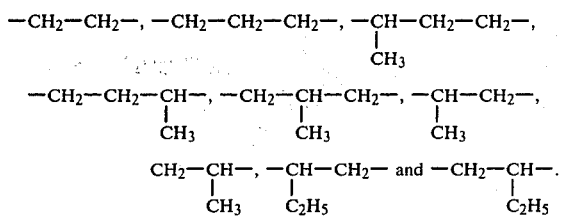

The present invention also relates to methods for the preparation of compounds of formula (I), and to methods for the control of dicotyledonous and certain monocotyledonous plant species using a herbicidally effective amount of a compound of formula (I).

Phenylurea compounds, which may be schematically illustrated by formula (II):

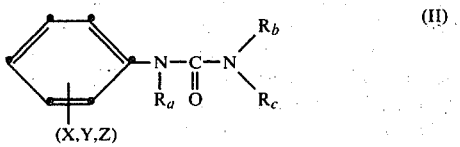

wherein $R_a$ to $R_c$ and X, Y and Z represent various substituents, are known to be herbicides, and a number of patents and published reports attest to their herbitoxic activity. Their use in agriculture is, however, quite limited, and is usually in preemergence applications.

Benzyloxyphenylureas, which may be illustrated by formula (III) below:

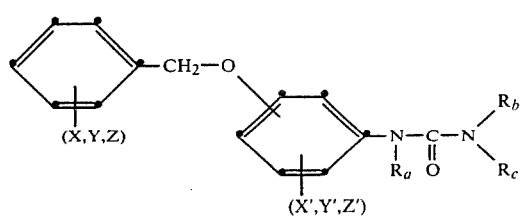

wherein X, X', Y, Y', Z, Z' and $R_a$ to $R_c$ are various substituents, are postemergence herbicides, but lack useful agronomic crop selectivity, nor is their herbicidal activity outstanding.

We now find that the novel phenylalkoxyphenylurea compounds of formula (I) of the present invention show not only excellent broadleaf weed control when applied postemergence, but also show an unexpected and useful degree of crop tolerance to wheat, barley, rice, corn, sorghum and soybeans. Crop selectivity may be further modified by applying these compounds to said crops at different growth stages. Additionally, some of the above compounds are also found to control grasses when applied postemergence at rates higher than those used for postemergence control of broadleaved weeds. Furthermore, the above compounds also control broadleaved weeds when applied preemergence.

The compounds of formula (I), wherein X is O and A is $C_1$–$C_6$ alkylene, may be conveniently prepared by the route shown below:

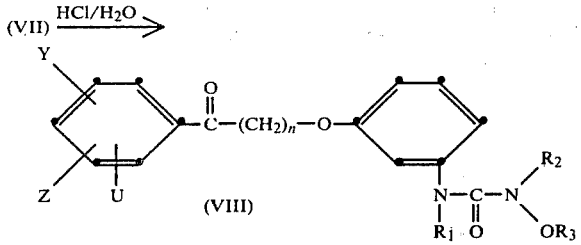

wherein Y, Z, U, $R_1$, $R_2$, $R_3$ and A are as hereinabove defined, L is selected from $OSO_2CH_3$ or halide. Thus, the appropriately substituted methanesulfonate ester of a phenylalkanol or the corresponding phenalkyl halide of formula (IV) is reacted with a ureidophenol of formula (V) in the presence of an organic or inorganic base, preferably potassium t-butoxide, and a solvent such as dimethylformamide (DMF) in the temperature range of from about 20° C. to about 90° C., and preferably 60° C. to 80° C., for a period of time sufficient to essentially complete the reaction. Hydroxyl groups in Y are preferably suitably protected in the course of this reaction.

Formula (I) compounds, in which the alkylene chain (A) is substituted, may be prepared as follows:

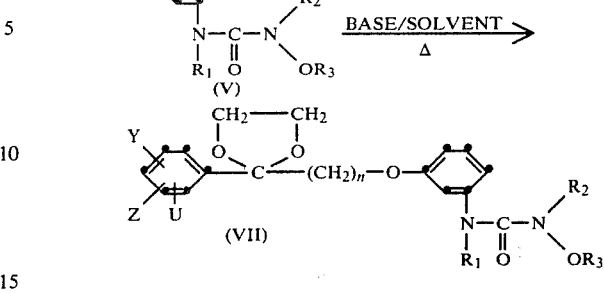

wherein Y, Z, U and $R_1$ to $R_3$ are as hereinabove defined, and n is an integer of from 1 to 5. The compound of formula (VII) is then hydrolyzed to yield the corresponding benzoylalkoxyphenylurea, as illustrated below:

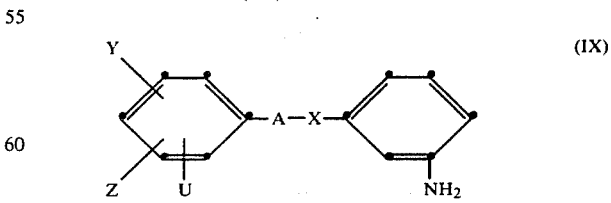

In the above-depicted sequence, the appropriately substituted 1,3-dioxolane of formula (VI) is reacted with a ureidophenol of formula (V) in the presence of an organic or inorganic base, preferably potassium t-butoxide and a solvent, such as DMF, in the temperature range of from about 20° C. to about 90° C., preferably 50° C. to 80° C., for a period of time sufficient to essentially complete the reaction. The thus-obtained urea of formula (VII) is then hydrolyzed with an aqueous acid, such as hydrochloric acid, to yield a benzoylalkoxyphenylurea of formula (VIII). The benzoylalkoxyphenylurea compounds of formula (VIII) obtained by the above procedure may be reduced by known procedures to the corresponding alcohols, and the latter are valuable intermediates for the preparation of formula (I) compounds in which the alkylene chain (A) is substituted, as defined above.

Compounds of formula (I) containing a formyl group in the $R_1$ or $R_3$ positions or a methyl group in the $R_1$ position are prepared from the appropriate aniline precursors of formula (IX):

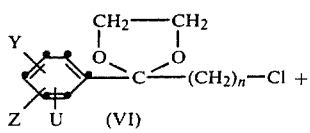

The above compounds may be obtained from the corresponding ureas by hydrolyzing same with 50% aqueous sodium hydroxide in n-butanol (3:11) at reflux for about 16 hours. Treating the above aniline (IX) with concentrated formic acid yields the formanilide (X):

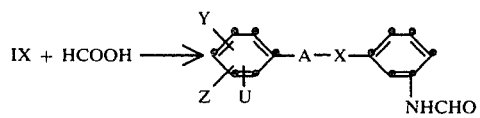

The formanilide (X) may be reduced, for instance, with lithium aluminum hydride, borane, and the like, to the corresponding N-methylaniline of formula (XI):

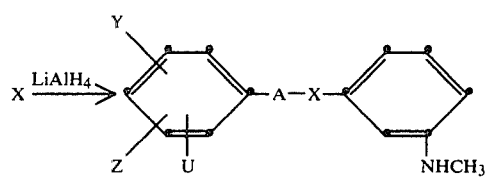

Compounds X and XI, when reacted with isocyanates yield formula (I) ureas, wherein $R_1$ is formyl or methyl, respectively.

Reacting the aniline (IX) with phosgene or thiophosgene yields the corresponding isocyanate or isothiocyanate (XII) which when reacted with the appropriately substituted alkoxyalkylamines affords formula (I) compounds, as shown below:

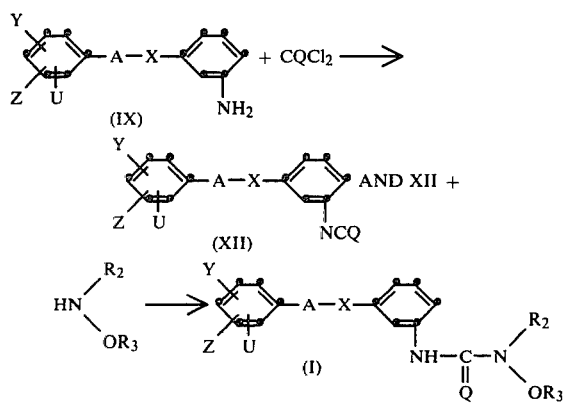

Formula (I) type compounds, wherein X is S, SO and $SO_2$, are prepared by a slightly different route, as shown below:

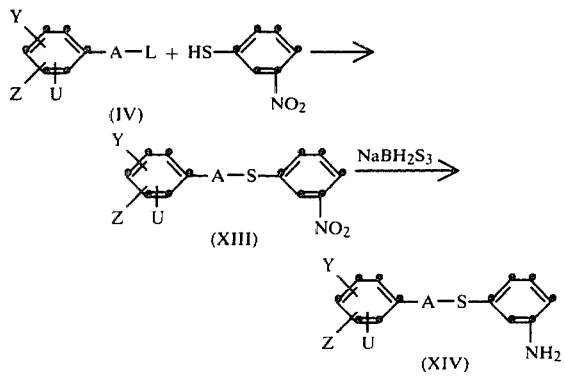

and

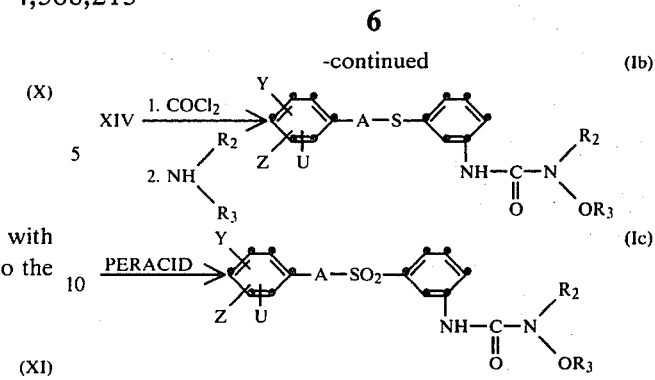

Accordingly, by the above route, m-nitrothiophenol is reacted with the appropriately substituted methanesulfonate ester of a phenylalkanol or the corresponding phenylalkyl halide of the formula (IV) in the presence of an organic or inorganic base, preferably potassium t-butoxide and a solvent, such as DMF, in the temperature range of from about 20° C. to about 90° C., and preferably 60° C. to 80° C., for a period of time sufficient to essentially complete the reaction. The nitro compound (XIII) obtained by the above reaction is then reduced with sulfurated sodium borohydride to afford the amine of formula (XIV) ($Y \neq NO_2$). This amine is then reacted with phosgene to yield the corresponding isocyanate which reacts with the appropriately substituted alkoxyalkylamines to afford a compound of formula (I) wherein X is S. Oxidation of this compound leads to the corresponding sulfoxide or sulfone, respectively.

The following formula (I) compounds which are of interest can be prepared by one or more of the above-depicted routes:

1-methoxy-1-methyl-3-[3-(3-phenylpropoxy)phenyl]-urea;
1-methoxy-1-methyl-3-[3-(3-phenylbutoxy)phenyl]-urea;
1-methoxy-1-methyl-3-[3-(1-methyl-3-phenyl-propoxy)-phenyl]urea;
1-methoxy-1-methyl-3-[3-(β-methylphenethyloxy)-phenyl]urea;
1-methoxy-1-methyl-3-[3-(α-methylphenethyloxy)-phenyl]urea;
3-[3-(3,4-dimethoxyphenethyloxy)phenyl]-1-methoxy-1-methylurea;
3-{3-[3-(4-methoxyphenyl)propoxy]phenyl}-1-methoxy-1-methylurea;
3-[3-(3-methoxyphenethyloxy)phenyl]-1-methoxy-1-methylurea;
3-[3-(4-chlorophenethyloxy)phenyl]-1-methoxy-1-methylurea;
3-[3-(2,6-dichlorophenethyloxy)phenyl]-1-methoxy-1-methylurea;
3-formyl-1-methoxy-3-[3-(phenethyloxy)phenyl]urea;
p0 1-methoxy-3-methyl-3-[3-(phenethyloxy)phenyl]urea;
1-methoxy-1-methyl-3-[3-(phenethylsulfonyl)phenyl]-urea;
1-methoxy-1-methyl-3-[3-(phenethylthio)phenyl]urea;
3-[3-(2-benzoylethoxy)phenyl]-1-methoxy-1-methylurea;
1-methoxy-1-methyl-3-{3-[2-(2-phenyl-1,3-dioxolan-2-yl)ethyloxy]phenyl}urea;
1-methoxy-1-methyl-3-[3-(phenacyloxy)phenyl]urea;

3-[3-(β-hydroxyphenethyloxy)phenyl]-1-methoxy-1-methylurea;
3-[3-β-chlorophenethyloxy)phenyl]-1-methoxy-1-methylurea;
3-[3-β-bromophenethyloxy)phenyl]-1-methoxy-1-methylurea;
3-[3-(β-methoxyphenethyloxy)phenyl]-1-methoxy-1-methylurea;
1-methoxy-1-methyl-3-[3-(β-methylthiophenethyloxy)phenyl]urea;
3-[3-(β-cyano-phenethyloxy)phenyl]-1-methoxy-1-methylurea;
1-methoxy-1-methyl-3-[3-(3-methylphenethyloxy)phenyl]urea;
3-[3-(2-methoxyphenethyloxy)phenyl]-1-methoxy-1-methylurea;
1-methoxy-1-methyl-3-[3-(3-nitrophenethyloxy)phenyl]urea;
3-[3-(2,4-dichlorophenethyloxy)phenyl]-1-methoxy-1-methylurea;
1-methoxy-1-methyl-3-[3-(2,6-dimethylphenethyloxy)phenyl]urea;
3-[3-(3-cyanophenethyloxy)phenyl]-1-methoxy-1-methylurea;
3-[3-(3-trifluoromethylphenethyloxy)phenyl]-1-methoxy-1-methylurea;
1-methoxy-1-methyl-3-[3-(3-methylsulfonylphenethyloxy)phenyl]urea;
3-[3-(4-formylaminophenethyloxy)phenyl]-1-methoxy-1-methylurea;
1-methoxy-1-methyl-3-[3-(2,4-dimethylphenethyl-oxy)phenyl]urea;
1-methoxy-1-methyl-3-[3-(β, 4-dimethylphenethyloxy)phenyl]urea;
1-methoxy-1-methyl-3-[3-(α,4-dimethylphenethyl-oxy)phenyl]urea;
3-[3-(4-methoxy-α-methylphenethyloxy)phenyl]-1-methoxy-1-methylurea;
3-[3-(4-methoxy-β-methylphenethyloxy)phenyl]-1-methoxy-1-methylurea;
3-[3-(3-methoxy-β-methylphenethyloxy)phenyl]-1-methoxy-1-methylurea;
3-[3-(β-ethyl-3-methoxyphenethyloxy)phenyl]-1-methoxy-1-methylurea;
3-[3-(β-ethyl-4-methoxyphenethyloxy)phenyl]-1-methoxy-1-methylurea;
3-[3(β-ethyl-4-methylphenethyloxy)phenyl]-1-methoxy-1-methylurea;
1-methoxy-1-methyl-3-[3-(β,β-dimethylphenethyloxy)phenyl]urea;
1-methoxy-1-methyl-3-[3-(α,β-dimethylphenethyloxy)phenyl]urea;
1-methoxy-1-methyl-3-[3-(3,3-diphenylpropoxy)phenyl]urea;
1-methoxy-1-1-methyl-3-[3-(2-methyl-3-phenylpropoxy)-phenyl]urea;
3-[3-(2-fluoro-3-phenylpropoxy)phenyl]-1-methoxy-1-methylurea;
3-[3-(2-bromo-3-phenylpropoxy)phenyl]-1-methoxy-1-methylurea;
3-[3-(2-methoxy-3-phenylpropoxy)phenyl]-1-methoxy-1-methylurea;
3-[3-(2-cyano-3-phenylpropoxy)phenyl]-1-methoxy-1-methylurea;
methanesulfonate of 3-[3-(4-hydroxyphenethyl-oxy)phenyl]-1-methoxy-1-methylurea;
1-methoxy-1-methyl-3-[3-(4-propoxyphenethyloxy)phenyl]urea;
3-[3-(4-ethoxyphenethyloxy)phenyl]-1-methoxy-1-methylurea;
3-[3-(4-acetoxyphenethyloxy)phenyl]-1-methoxy-1-methylurea;
1-methoxy-1-methyl-3-{3-[4-(2-propynyloxy)phenethyloxy]phenyl}urea;
3-[3-(4-allyloxyphenethyloxy)phenyl]-1-methoxy-1-methylurea;
3-{3-[4-(carboethoxymethoxy)phenethyloxy]phenyl}-1-methoxy-1-methylurea;
3-[3-(4-benzyloxyphenethyloxy)phenyl]-1-methoxy-1-methylurea;
1-methoxy-1-methyl-3-[3-(4-methylcabamoyloxyphenethyloxy)phenyl]urea;
3-[3-(4-t-butylcarbamoyloxyphenethyloxy)phenyl]-1-methoxy-1-methylurea;
1-methoxy-1-methyl-3-[3-(3-nitrophenethyloxy)phenyl]urea;
1-methoxy-1-methyl-3-[3-(4-nitrophenethyloxy)phenyl]urea;
1-methoxy-1-methyl-3-{3-[3-(2-nitrophenyl)propoxy]phenyl}urea;
1-methoxy-1-methoxy-3-{3-[3-(3-nitrophenyl)propoxy]phenyl}urea;
1-methoxy-1-methyl-3-[3-(β-methyl-4-nitrophenethyloxy)phenyl]urea;
1-methoxy-1-methyl-3-[3-(phenethyloxy)phenyl]-thiourea;
3-[3-(4-methoxyphenethyloxy)phenyl]-1-methoxy-1-methylthiourea;
1-methoxy-1-methyl-3-[3-(4-methylphenethyloxy)phenyl]thiourea;
1-methoxy-1-methyl-3-[3-(β-methylphenethyloxy)phenyl]thiourea;
1-methoxy-1-methyl-3-[3-(β,4-dimethylphenethyl-oxy)phenyl]thiourea;
3-[3-(4-isopropenyl-β-methylphenethyloxy)phenyl-1-methoxy-1-methylurea;
1-methoxy-1-methyl-3-[3-(4-vinylphenethyloxy)phenyl]urea;
1-methoxy-1-methyl-3-[3-(β-methylcarbamoyloxyphenethyloxy)phenyl]urea;
3-[3-(β-methanesulfonylphenethyloxy)phenyl]-1-methoxy-1-methylurea;
1-methoxy-1-methyl-3-[3-(β-carbomethoxyphenethyloxy)phenyl]urea;
3-[3-(2,4,6-tribromophenethyloxy)phenyl]-1-methoxy-1-methylurea;
3-[3-(2,4,6-trichlorophenethyloxy)phenyl]-1-methoxy-1-methylurea;
1-methoxy-1-methyl-3-[3-(3,4,5-trimethoxyphenethyloxy)phenyl]urea;
3-[3-(2,6-dichloro-4-trifluoromethylphenethyl-oxy)phenyl]-1-methoxy-1-methylurea;
1-methoxy-1-methyl-3-[3-(2,4,5-trimethylphenethyloxy)phenyl]urea;
3-[3-(2,4-dichloro-5-nitrophenethyloxy)phenyl]-1-methoxy-1-methylurea;
3-[3-(4-acetylphenethyloxy)phenyl]-1-methoxy-1-methylurea;
3-[3-(4-difluoromethoxyphenethyloxy)phenyl-1-methoxy-1-methylurea;
3-[3-(4-trifluoromethoxyphenethyloxy)phenyl]-1-methoxy-1-methylurea;
3-[3-(4-chlorodifluoromethoxyphenethyloxy)phenyl]-1-methoxy-1-methylurea; and
1-methoxy-1-methyl-3-[3-(β-nitrophenethyloxy)phenyl]urea.

As stated above, formula (I) compounds of the present invention show excellent postemergence herbicidal activity coupled with good crop selectivity in the presence of barley, wheat, rice, sorghum, corn and soybeans.

In practice, the active compounds are generally formulated as dusts, dust concentrates, wettable powders, emulsion concentrates, flowable concentrates, and the like.

Dusts can be prepared by grinding about 1% to 15% by weight of active compound with about 99% to 85% by weight of an inert diluent, such as attaclay, montmorillonite, diatomaceous earth, kaolin, pumice, talc, and the like.

Dust concentrates are made in a similar fashion, excepting that percent by weight of active ingredient is increased to about 16% to 75% of the composition.

Wettable powders are prepared in the same manner as dust concentrates, but usually contain, in addition to the active ingredient and solid diluent, from about 1% to 5% by weight of a wetting agent, such as sodium isopropylnaphthalene sulfonate or the sodium salt of a sulfonated naphthalene formaldehyde condensate, and from about 1% to 5% by weight of a dispersing agent, such as hydroxyethyl cellulose. A typical formulation would be 50% by weight of active ingredient, 2% of dispersing agent, 5% of wetting agent and 43% attapulgite.

Emulsion concentrates are prepared by dissolving 15% to 70% by weight of the compound in 85% to 30% by weight of a solvent, such as benzene, toluene, xylene, kerosene, 2-methoxyethanol, propylene glycol, diethylene glycol, diethylene glycol monomethyl ether, formamide, N-methylpyrrolidone, methylformamide, and the like, and mixtures thereof. Advantageously, surfactants, such as polyoxyethylated vegetable oil or an alkyl phenoxy polyoxyethylene ethanol, are also incorporated in amounts of 1% to 5% by weight of said concentrate.

In using wettable powders, emulsion concentrates or flowable concentrates, the formulated material is generally dispersed in water and applied at the rate of from about 0.06 kg per hectare to about 2 kg per hectare to the plants, or to soil containing the seeds of said plants.

The invention is further illustrated by the following examples, which are not to be taken as being limitative thereof.

EXAMPLE 1

Preparation of 1-Methoxy-1-methyl-3-[3-(4-methylphenethyloxy)-phenyl]urea

A mixture of 3-(3-hydroxyphenyl)-1-methoxy-1-methylurea (3.50 g; 0.0178 mol), dimethylformamide (DMF; 150 ml) and potassium t-butoxide (2.0 g; 0.018 mol) is stirred for 30 minutes under a nitrogen atmosphere. Next, the 4-methylphenethyl ester of methanesulfonic acid (3.82 g; 0.018 mol) is added to the above, and the reaction mixture stirred for 21 hours at 65° C. The solvent (DMF) is then removed under vacuum, the residue shaken with ether (500 ml) and filtered. The ethereal solution is stripped to give 10 g of a tan solid. This solid is purified by column chromatography using basic alumina and hexane:ethyl acetate (1:1) eluent. The eluate is evaporated to afford 4.9 g of light yellow solid. The solid is recrystallized from a mixture of hexane and ethyl acetate (3:1) to afford 2.57 g of title product, melting point 108°–109° C.

EXAMPLE 2

Preparation of Alkoxyalkyl-phenylalkoxyalkyl Urea Compounds

By the method of Example 1, the compounds shown in Table I are prepared.

TABLE I

[Structure: substituted diphenyl compound with U, Y, Z substituents on one ring, A—X linker, and NH—C(=O)—N(CH₃)(OCH₃) group on the other ring]

| No. | U | Y | Z | A—Z | Melting Point °C. | Recrystallization Solvent | Analysis Calculated (%) | Found |
|---|---|---|---|---|---|---|---|---|
| 1 | H | H | H | —CH₂CH₂—O— | 82–83 | Methylcyclohexane-ethyl acetate (19:1) | C, 67.98<br>H, 6.71<br>N, 9.33 | 67.83<br>6.87<br>9.33 |
| 2 | H | 4-OCH₃ | H | —CH₂CH₂—O— | 73–74 | Methylcyclohexane-ethyl acetate (10:1) | C, 65.44<br>H, 6.91<br>N, 8.48 | 64.94<br>6.87<br>8.33 |
| 3 | H | 4-CH₃ | H | —CH₂CH₂—O— | 108–109 | Hexane-ethyl acetate (3:1) | C, 68.77<br>H, 7.05<br>N, 8.91 | 68.53<br>7.31<br>8.86 |
| 4 | H | 3-OCH₃ | H | —CH₂CH₂—O— | 58–59 | Methylcyclohexane-ethyl acetate (9:1) | C, 65.44<br>H, 6.71<br>N, 8.48 | 65.39<br>7.02<br>8.52 |
| 5 | H | H | H | —CH(C₂H₅)CH₂—O— | 60.5–62 | Methylcyclohexane | C, 69.49<br>H, 7.37<br>N, 8.53 | 70.28<br>7.87<br>8.46 |

EXAMPLE 3

General Procedure for the Preparation of Esters of Methanesulfonic Acid

A solution of the appropriate alcohol (0.1 mol) and triethylamine (0.15 mol) in methylene chloride (150 ml) is rapidly stirred, chilled to −15° C. and methanesulfonyl chloride (0.11 mol) added at a rate to maintain the reaction temperature below −10° C. After the addition is completed, the solution is stirred for 30 minutes in the cold and then at room temperature for 2 hours. Next, the methylene chloride solution is separated, washed with ice-cold water, ice-cold 10% hydrochloric acid, saturated sodium bicarbonate solution, saturated brine, and then dried over sodium sulfate. Finally, the appropriate ester is isolated by evaporating the methylene chloride solution under vacuum.

Esters of methanesulfonic acid prepared by the above procedure are listed in Table II below, together with their physical data, when such is available.

TABLE II $$\text{[benzene ring]}-A-OSO_2CH_3$$
with substituents Y, Z

| No. | Y | Z | A | Melting Point °C. | Analysis Calculated (%) | Found | Remarks |
|-----|---|---|---|---|---|---|---|
| 1 | p-CH$_3$ | H | CH$_2$—CH$_2$ | 50–52 | C, 56.05 | 55.80 | |
|   |   |   |   |   | H, 6.58 | 6.71 | |
|   |   |   |   |   | S, 14.96 | 14.71 | |
| 2 | H | H | CH$_3$ \| CH$_2$—CH | straw oil | C, 56.05 | 56.12 | |
|   |   |   |   |   | H, 6.58 | 6.76 | |
|   |   |   |   |   | S, 14.96 | 15.18 | |
| 3 | p-Cl | H | CH$_2$—CH$_2$ | 40–44 | C, 46.05 | 46.50 | |
|   |   |   |   |   | H, 4.73 | 4.89 | |
|   |   |   |   |   | S, 13.66 | 13.60 | |
|   |   |   |   |   | Cl, 15.11 | 15.32 | |
| 4 | H | H | (CH$_2$)$_4$ | straw oil | C, 57.87 | 58.70 | |
|   |   |   |   |   | H, 7.07 | 7.36 | |
|   |   |   |   |   | S, 14.05 | 13.75 | |
| 5 | p-F | H | CH$_2$—CH$_2$ | brown oil | C, 49.53 | 49.82 | |
|   |   |   |   |   | H, 5.08 | 5.04 | |
|   |   |   |   |   | S, 8.73 | 8.60 | |
|   |   |   |   |   | F, 14.69 | 14.69 | |
| 6 | H | H | CH$_3$ \| CH—CH$_2$ | amber oil | | | Lit. J.O.C. 38(8) 1518 (1973) |
| 7 | H | H | (CH$_2$)$_3$ | amber oil | C, 56.04 | 55.98 | |
|   |   |   |   |   | H, 6.54 | 6.71 | |
|   |   |   |   |   | S, 14.96 | 14.94 | |
| 8 | H | H | (CH$_2$)$_5$ | amber oil | C, 54.48 | 54.72 | |
|   |   |   |   |   | H, 7.49 | 7.86 | |
|   |   |   |   |   | S, 13.23 | 13.08 | |
| 9 | H | H | CH$_2$—CH$_2$ | amber oil | | | Lit. J.O.C. 38(8) 1518 (1973) |
| 10 | p-OCH$_3$ | H | CH$_2$—CH$_2$ | yellow oil | C, 52.15 | 51.49 | |
|   |   |   |   |   | H, 6.13 | 5.92 | |
|   |   |   |   |   | S, 13.93 | 13.36 | |
| 11 | H | H | CH$_3$ \| CH$_2$CH$_2$CH | straw oil | C, 57.87 | 57.23 | |
|   |   |   |   |   | H, 7.07 | 7.14 | |
|   |   |   |   |   | S, 14.05 | 12.96 | |
| 12 | H | H | C$_2$H$_5$ \| CH—CH$_2$ | brown oil | C, 57.87 | 57.91 | |
|   |   |   |   |   | H, 7.07 | 7.19 | |
|   |   |   |   |   | S, 14.05 | 13.97 | |
| 13 | p-NO$_2$ | H | CH$_2$—CH$_2$ | 80.5–82.5 | | | J.O.C. 38(8) 1518 (1973) Lit. 80–81° C. |
| 14 | p-OCH$_3$ | m-OCH$_3$ | CH$_2$—CH$_2$ | yellow oil | C, 50.75 | 50.42 | |
|   |   |   |   |   | H, 6.20 | 5.74 | |
|   |   |   |   |   | S, 12.32 | 12.23 | |
| 15 | H | H | C$_2$H$_5$ \| CH$_2$—CH | brown oil | C, 57.87 | 58.03 | |
|   |   |   |   |   | H, 7.07 | 7.21 | |
|   |   |   |   |   | S, 14.05 | 13.86 | |
| 16 | H | H | CH$_3$ \| CH—CH$_2$—CH$_2$ | | C, 58.87 | 58.17 | |
|   |   |   |   |   | H, 7.07 | 7.38 | |
|   |   |   |   |   | S, 14.05 | 13.88 | |
| 17 | 3-Cl | 4-Cl | CH$_2$CH$_2$ | orange oil | C, 40.16 | 40.28 | |
|   |   |   |   |   | H, 3.75 | 3.95 | |
|   |   |   |   |   | S, 11.91 | 11.75 | |
|   |   |   |   |   | Cl, 26.35 | 26.35 | |
| 18 | 2-Cl | 6-Cl | CH$_2$CH$_2$ | 64–67 | C, 40.16 | 40.57 | |
|   |   |   |   |   | H, 3.75 | 3.94 | |
|   |   |   |   |   | S, 11.91 | 11.68 | |
|   |   |   |   |   | Cl, 26.35 | 26.21 | |
| 19 | 3-CH$_3$O | H | CH$_2$CH$_2$ | light orange oil | C, 52.15 | 51.97 | |
|   |   |   |   |   | H, 6.13 | 6.19 | |
|   |   |   |   |   | S, 13.93 | 13.70 | |
| 20 | 2-Cl | 4-Cl | CH$_2$CH$_2$ | oil | C, 40.16 | 40.35 | |
|   |   |   |   |   | H, 3.75 | 3.82 | |
|   |   |   |   |   | S, 11.91 | 11.70 | |
|   |   |   |   |   | Cl, 26.35 | 26.16 | |
| 21 | 4-CH$_3$O | H | CH$_2$CH$_2$CH$_2$ | 41–43 | C, 54.08 | 54.06 | |

TABLE II-continued

[Structure: benzene ring with substituents Y, Z, and —A—OSO₂CH₃]

| No. | Y | Z | A | Melting Point °C. | Analysis Calculated (%) | Found | Remarks |
|---|---|---|---|---|---|---|---|
| | | | | | H, 6.60 | 6.82 | |
| | | | | | S, 13.13 | 14.27 | |

EXAMPLE 4

Esters of Methanesulfonic Acid

By the method of Example 3, the following esters of methanesulfonic acid can be prepared:

2,4-dimethylphenethyl alcohol methanesulfonate;
2-methoxyphenethyl alcohol methanesulfonate;
4-hydroxyphenethyl alcohol bis(methanesulfonate);
2,4,6-tribromophenethyl alcohol methanesulfonate;
2,4,6-trichlorophenethyl alcohol methanesulfonate;
3,4,5-trimethoxyphenethyl alcohol methanesulfonate;
2,6-dichloro-4-trifluoromethylphenethyl alcohol methanesulfonate;
2,4,5-trimethylphenethyl alcohol methanesulfonate;
2,4-dichloro-5-nitrophenethyl alcohol methanesulfonate;
4-acetylphenethyl alcohol methanesulfonate;
4-difluoromethoxyphenethyl alcohol methanesulfonate;
4-chlorodifluoromethoxyphenethyl alcohol methanesulfonate;
β-chlorophenethyl alcohol methanesulfonate;
β-fluorophenethyl alcohol methanesulfonate;
β-methoxyphenethyl alcohol methanesulfonate;
β-cyanophenethyl alcohol methanesulfonate;
β-methanesulfonylphenethyl alcohol methanesulfonate;
β-methylthiophenethyl alcohol methanesulfonate;
β-nitrophenethyl alcohol methanesulfonate;
β-trifluoromethylphenethyl alcohol methanesulfonate;
2-formamido-3-phenylpropan-1-ol methanesulfonate;
2,3-dichloro-3-phenylpropan-1-ol methanesulfonate;
2-methoxy-3-phenylpropan-1-ol methanesulfonate;
4-carboethoxyphenethyl alcohol methanesulfonate;
4-isopropenyl-β-methylphenethyl alcohol methanesulfonate;
4-vinylphenethyl alcohol methanesulfonate;
4-allylphenethyl alcohol methanesulfonate;
N-methylcarbamic acid ester of 3-hydroxy-3-phenylpropan-1-ol methanesulfonate;
3-acetoxy-3-phenylpropan-1-ol methanesulfonate;
3-methyleneoxycarboxymethyl-3-phenylpropan-1-ol methanesulfonate;
3-methanesulfonyl-3-phenylpropan-1-ol methanesulfonate;
β-carbomethoxyphenethyl alcohol methanesulfonate;
2-cyano-3-phenylpropan-1-ol methanesulfonate;
2-chloro-3-phenylpropan-1-ol methanesulfonate;
β-methoxy-4-methylphenethyl alcohol methanesulfonate;
β-chloro-4-methoxyphenethyl alcohol methanesulfonate;
4-methyl-β-nitrophenethyl alcohol methanesulfonate;
β,4-dimethylphenethyl alcohol methanesulfonate;
β,4-dimethoxyphenethyl alcohol methanesulfonate;
α,4-dimethylphenethyl alcohol methanesulfonate; and
3-(4-methoxyphenyl)buten-1-ol methanesulfonate.

EXAMPLE 5

The postemergence herbicidal activity of the compounds of the present invention is demonstrated by the following tests, wherein a variety of monocotyledonous and dicotyledonous plants are treated with test compounds dispersed in aqueous acetone mixtures. In the tests, seedling plants are grown in separate cups for about two weeks. The test compounds are dispersed in 50/50 acetone/water mixtures containing 0.5% TWEEN ® 20, a polyoxyethylene sorbitan monolaurate surfactant of Atlas Chemical Industries, in sufficient quantity to provide the equivalent of about 0.063 kg to 2.0 kg per hectare of active compound when applied to the plants through a spray nozzle operating at 2.81 kg/cm² pressure for a predetermined time. After spraying, the plants are placed on greenhouse benches and are cared for in the usual manner, commensurate with conventional greenhouse practices. Two weeks after treatment, the seedling plants are examined and rated according to the rating system provided below. The data obtained are reported in Table III below, wherein it can be seen that the compounds of the present invention selectively control broadleaved weeds in the presence of crops.

| RATING SYSTEM | |
|---|---|
| Rating: | % Control (Compared to Check) |
| 9 - Complete kill | 100 |
| 8 - Approaching complete kill | 91–99 |
| 7 - Good herbicidal effect | 80–90 |
| 6 - Herbicidal effect | 65–79 |
| 5 - Definite injury | 45–64 |
| 4 - Injury | 30–44 |
| 3 - Moderate effect | 10–29 |
| 2 - Slight effect | 6–15 |
| 1 - Trace effect | 1–5 |
| 0 - No effect | 0 |
| X - Missing data | — |

The above rating scale is based upon a visual observation of plant stand, vigor, malformation, size, chlorosis, and overall plant appearance as compared with a control.

A rating of "X" is given if effects on plant growth caused by chemical treatment cannot be clearly determined as a result of disease, failure to germinate or grow or where the plants were not present in a particular test at a particular rate because of shortage of plant material.

| Plant Abbreviations | | |
|---|---|---|
| Code | Common Name | Scientific Name |
| BA | Barnyardgrass | *Echinochloa crusgalli* |
| FO | Green Foxtail | *Setaria viridis* |
| WO | Wild Oats | *Avena fatua* |
| CB | Cocklebur | *Xanthium pensylvanicum* |
| JW | Jimsonweed | *Datura stramonium* |
| LA | Lambsquarters | *Chenopodium album* |

-continued

| Plant Abbreviations | | |
|---|---|---|
| Code | Common Name | Scientific Name |
| MG | Morningglory | *Ipomoea spp.* |
| MU | Mustard | *Brassica kaber* |
| PI | Pigweed | *Amaranthus retroflexus* |
| RW | Ragweed | *Ambrosia artemisiifolia* |
| VL | Velvetleaf | *Abutilon theophrasti* |
| BY | Barley | *Hordeum vulgare* |
| CN | Corn | *Zea mays* |
| RI | Rice | *Oryza sativa* |
| SO | Sorghum | *Sorghum bicolor* |
| SY | Soybeans | *Glycine max* |
| WH | Wheat | *Triticum aestivum* |

TABLE III

Evaluation of the Postemergence Herbicidal Activity of Compounds of the Invention in the Presence of Agronomic Crops

| Compound | Rate kg/ha | BA | FO | WO | CB | JW | LA | MG | MU | PI | RW | VL | BY | CN | RI | SO | SY | WH |
|---|---|---|---|---|---|---|---|---|---|---|---|---|---|---|---|---|---|---|
| 1-methoxy-1-methyl-3-[3-(phenethyloxy)phenyl]urea | 2.0 | 4 | 7 | 7 | 9 | 9 | 9 | 9 | 9 | 9 | 9 | 9 | 6 | 9 | 6 | 9 | 9 | 8 |
| | 1.0 | 3 | 5 | 6 | 9 | 9 | 9 | 9 | 9 | 9 | 9 | 9 | 3 | 7 | 3 | 8 | 9 | 4 |
| | 0.50 | 1 | 3 | 3 | 9 | 1 | 9 | 9 | 9 | 9 | 9 | 9 | 2 | 9 | 2 | 6 | 7 | 2 |
| | 0.25 | 0 | 1 | 1 | 9 | — | 9 | 9 | 9 | 9 | 9 | 3 | 1 | 4 | 1 | 3 | 8 | 1 |
| | 0.125 | 0 | 1 | 0 | 9 | 0 | 9 | 9 | 8 | 8 | 7 | 9 | 0 | 1 | 0 | 2 | 3 | 1 |
| | 0.063 | 0 | 0 | 0 | 9 | 0 | 9 | 3 | 7 | 8 | 6 | 2 | 0 | 1 | 0 | 1 | 2 | 0 |
| 1-methoxy-1-methyl-3-[3-(4-methylphenethyloxy)phenyl]urea | 2.0 | 1 | 0 | 3 | 9 | 9 | 9 | 9 | 9 | 9 | 9 | 8 | 0 | 4 | 2 | 0 | 2 | 0 |
| | 1.0 | 0 | 0 | 1 | 9 | 9 | 8 | 9 | 9 | 8 | 9 | 8 | 0 | 7 | 1 | 0 | 1 | 0 |
| | 0.50 | 0 | 0 | 0 | 9 | 0 | 8 | 9 | 9 | 7 | 6 | 7 | 0 | 2 | 0 | 0 | 1 | 0 |
| | 0.25 | 0 | 0 | 0 | 3 | 0 | 6 | 3 | 9 | 0 | 6 | 6 | 0 | 1 | 0 | 0 | — | 0 |
| | 0.125 | 0 | 0 | 0 | 0 | 0 | 0 | 0 | 5 | 0 | 0 | 0 | 0 | 0 | 0 | 0 | 1 | 0 |
| | 0.063 | 0 | 0 | 0 | 0 | 0 | 0 | 0 | 0 | 0 | 0 | 0 | 0 | 0 | 0 | 0 | 0 | 0 |
| 1-methoxy-1-methyl-3-[3-(4-methoxyphenethyloxy)phenyl]urea | 2.0 | 2 | 4 | 6 | 9 | 9 | 9 | 9 | 9 | 9 | 9 | 9 | 3 | 9 | 1 | 9 | 9 | 3 |
| | 1.0 | 1 | 3 | 2 | 9 | 9 | 9 | 9 | 9 | 9 | 9 | 9 | 2 | 5 | 2 | 8 | 7 | 2 |
| | 0.50 | 1 | 3 | 1 | 9 | 2 | 9 | 9 | 9 | 9 | 7 | 6 | 0 | 4 | 1 | 3 | 3 | 0 |
| | 0.25 | 1 | 1 | 0 | 9 | × | 9 | 9 | 7 | 9 | 6 | 6 | 0 | 3 | 0 | 2 | 2 | 0 |
| | 0.125 | 0 | 0 | 0 | 9 | 0 | 9 | 9 | 7 | 9 | 6 | 6 | 0 | 2 | 0 | 0 | 1 | 0 |
| | 0.063 | 0 | 0 | 0 | 9 | 0 | 3 | 6 | 7 | 0 | 6 | 6 | 0 | 0 | 0 | 0 | 0 | 0 |

| Compound | Rate kg/ha | BA | FO | WO | CB | JW | LA | MG | MU | PI | RW | VL | BY | CN | RI | SO | WY | WH |
|---|---|---|---|---|---|---|---|---|---|---|---|---|---|---|---|---|---|---|
| 1-methoxy-1-methyl-3-[3-(3-methoxyphenethyloxy)phenyl]urea | 2.0 | 4 | 9 | 1 | 9 | 9 | 9 | 9 | 9 | 9 | 9 | 9 | 0 | 8 | 0 | 1 | 9 | 0 |
| | 1.0 | 4 | 6 | 1 | 0 | 9 | 9 | 9 | 9 | 9 | 9 | 9 | 0 | 9 | 2 | 9 | 9 | 0 |
| | 0.50 | 1 | 1 | 0 | × | 9 | 9 | 9 | 9 | 9 | 8 | 9 | 0 | 9 | 4 | 1 | 9 | 0 |
| | 0.25 | 0 | 0 | 0 | 0 | 0 | 9 | 9 | 9 | 9 | 2 | 9 | 0 | 0 | 3 | 9 | 0 | 0 |
| | 0.125 | 0 | 0 | 0 | 0 | 0 | 3 | 0 | 0 | 9 | 0 | 0 | 0 | 0 | 0 | 9 | 0 | 0 |
| | 0.063 | 0 | 0 | 0 | × | × | × | × | × | × | × | × | × | × | × | × | × | × |
| 1-methoxy-1-methyl-3-[3-(β-ethylphenethyloxy)phenyl]urea | 2.0 | × | 6 | 0 | 0 | 9 | 9 | 9 | 9 | 6 | 8 | 9 | 0 | 1 | 2 | 9 | 9 | 0 |
| | 1.0 | 4 | 0 | 0 | 0 | 6 | 9 | 9 | 9 | 4 | 9 | 9 | 0 | 0 | 0 | 4 | 0 | 0 |
| | 0.50 | 0 | 0 | 0 | 0 | 6 | 9 | 9 | 9 | 4 | 3 | 9 | 0 | 0 | 0 | 0 | 0 | 0 |
| | 0.25 | 0 | 0 | 0 | 0 | 2 | 9 | 0 | 9 | 0 | 0 | 0 | 0 | 0 | 0 | 0 | 0 | 0 |
| | 0.125 | 0 | 0 | 0 | 0 | 0 | 2 | 0 | 8 | 0 | 0 | 0 | 0 | 0 | 0 | 0 | 0 | 0 |
| | 0.063 | 0 | 0 | 0 | 0 | 0 | 0 | 0 | 0 | 0 | 0 | 0 | 0 | 0 | 0 | 0 | 0 | 0 |

EXAMPLE 6

Preemergence Herbicidal Activity

The preemergence herbicidal activity of the compounds of the present invention is exemplified by the following tests in which seeds or propagating organs of a variety of monocotyledonous and dicotyledonous plants are separately mixed with potting soil and planted on top of approximately 2.5 cm of soil in separate cups or planted on soil surface and covered with approximately 1.25 cm of soil. After planting, the cups are sprayed with the selected aqueous acetone solution containing test compound in sufficient quantity to provide the equivalent of about 0.06 to 2.0 kg hectare of test compound per cup. The treated cups are then placed on greenhouse benches, watered and cared for in accordance with conventional greenhouse procedures. Three to five weeks after treatment, the tests are terminated and each cup is examined and rated according to the rating system set forth in Example 5. The data obtained are reported in Table IV below, wherein it can be seen that the compounds of the invention selectively control broadleaved weeds in the presence of crops when applied preemergence.

TABLE IV

Evaluation of the Preemergence Herbicidal Activity of Compounds of the Invention in the Presence of Agronomic Crops

| Compound | Rate kg/ha | BA | FO | WO | CB | JW | LA | MG | MU | PI | RW | VL | BY | CN | RI | SO | SY | WH |
|---|---|---|---|---|---|---|---|---|---|---|---|---|---|---|---|---|---|---|
| 1-methoxy-1-methyl-3-[3-(phen-ethyloxy)phenyl]urea | 2.0 | 3 | 6 | 7 | 8 | 9 | 9 | 4 | 9 | 9 | 3 | 9 | 0 | 0 | 0 | 0 | 0 | 2 |
| | 1.0 | 1 | 2 | 7 | 0 | 9 | 9 | 0 | 9 | 9 | 0 | 9 | 0 | 0 | 0 | 0 | 0 | 6 |
| | 0.50 | 0 | 0 | 7 | 0 | 9 | 9 | 0 | 8 | 9 | 0 | 0 | 0 | 0 | 0 | 0 | 0 | 0 |
| | 0.25 | 0 | 0 | 7 | 0 | 9 | 8 | 0 | 8 | 9 | 0 | 0 | 0 | 0 | 0 | 0 | 0 | 0 |
| | 0.125 | 0 | 0 | 4 | 0 | 9 | 7 | 0 | 1 | 3 | 0 | 0 | 0 | 0 | 0 | 0 | 0 | 0 |
| | 0.063 | 1 | 0 | 4 | 0 | 9 | 2 | 0 | 0 | 0 | 1 | 0 | 0 | 0 | 3 | 0 | 0 | 0 |
| 1-methoxy-1-methyl-3-[3-(4-methylphenethyloxy)phenyl]urea | 2.0 | 0 | 0 | 0 | 0 | 0 | 9 | 0 | 9 | 9 | 0 | 0 | 0 | 0 | 0 | 0 | 0 | 0 |
| | 1.0 | 0 | 0 | 0 | 0 | 0 | 9 | 0 | 9 | 9 | 0 | 0 | 0 | 0 | 0 | 0 | 0 | 0 |
| | 0.5 | 0 | 0 | 0 | 0 | 0 | 9 | 0 | 9 | 9 | 0 | 0 | 0 | 0 | 0 | 0 | 1 | 0 |
| | 0.25 | 0 | 0 | 0 | 0 | 0 | 9 | 0 | 4 | 8 | 0 | 0 | 0 | 0 | 0 | 0 | 0 | 0 |
| | 0.125 | 0 | 0 | 0 | 0 | 0 | 2 | 0 | 0 | 9 | 0 | 0 | 0 | 0 | 0 | 0 | 0 | 0 |
| | 0.063 | 0 | 0 | 0 | 0 | 0 | 9 | 9 | 0 | 9 | 0 | 9 | 0 | 0 | 0 | 0 | 0 | 0 |
| 1-methoxy-1-methyl-3-[3-(4-methoxyphenethyloxy)phenyl]urea | 2.0 | 8 | 9 | 7 | 9 | 9 | 9 | 2 | 9 | 9 | 7 | 9 | 0 | 0 | 0 | 0 | 0 | 0 |
| | 1.0 | 2 | 1 | 1 | 1 | 9 | 9 | 0 | 9 | 9 | 1 | 1 | 0 | 0 | 1 | 0 | 0 | 0 |
| | 0.50 | 0 | 0 | 0 | 0 | 9 | 9 | 0 | 2 | 9 | 0 | 0 | 0 | 0 | 4 | 0 | 0 | 0 |
| | 0.25 | 0 | 0 | 0 | 0 | 9 | 9 | 0 | 0 | 7 | 0 | 0 | 0 | 0 | 0 | 0 | 0 | 0 |
| | 0.125 | 0 | 0 | 0 | 0 | 0 | 7 | 0 | 0 | 4 | 0 | 0 | 0 | 0 | 0 | 0 | 0 | 0 |
| | 0.063 | 0 | 0 | 0 | 0 | 0 | 4 | 0 | 0 | 0 | 0 | 0 | 0 | 0 | 0 | 0 | 0 | 0 |
| 1-methoxy-1-methyl-3-(3-methoxyphenethyloxy)phenyl]urea | 2.0 | 7 | 8 | 8 | 0 | 9 | 9 | 0 | 9 | 9 | 8 | 0 | 0 | 0 | 0 | 0 | 0 | 0 |
| | 1.0 | 1 | 4 | 1 | 1 | 6 | 9 | 1 | 9 | 9 | 1 | 1 | 0 | 0 | 0 | 0 | 0 | 0 |
| | 0.50 | 0 | 1 | 0 | 0 | 0 | 9 | 0 | 8 | 8 | 0 | 0 | 0 | 0 | 0 | 0 | 0 | 0 |
| | 0.25 | 0 | 0 | 0 | 0 | 0 | 8 | 0 | 4 | 8 | 0 | 0 | 0 | 0 | 0 | 0 | 0 | 0 |
| | 0.125 | 0 | 0 | 0 | 0 | 0 | 3 | 0 | 0 | 0 | 0 | 0 | 0 | 0 | 0 | 0 | 0 | 0 |
| | 0.063 | 0 | 0 | 0 | 0 | 0 | 0 | 0 | 0 | 0 | 0 | 0 | 0 | 0 | 0 | 0 | 0 | 0 |

We claim:

1. A compound of formula:

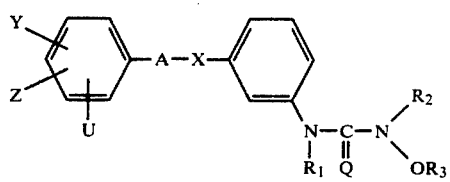

wherein X is selected from O, S, SO and SO$_2$; Q is O or S; Y is selected from the group consisting of hydrogen, halogen, C$_1$-C$_4$ alkyl, C$_2$-C$_5$ alkenyl, C$_2$-C$_5$ alkynyl, C$_1$-C$_4$ alkoxy, CH$_3$S, CH$_3$SO$_2$, CF$_3$, CN, NO$_2$, NH$_2$, C$_1$-C$_3$ alkylamino, $$NHCHO, \overset{O}{\underset{\|}{RO-C-}}, \overset{O}{\underset{\|}{R-C-O-}}, \overset{O}{\underset{\|}{CH_2-C-OR,}}$$

$$\overset{O}{\underset{\|}{R-NH-C-O,}} OH, OSO_2CH_3, OCF_2H, OCF_3 \text{ and } OCF_2Cl;$$

Z is selected from the group consisting of hydrogen, C$_1$-C$_4$ alkyl, C$_1$-C$_4$ alkoxy, halogen, CF$_3$ and NO$_2$; U is hydrogen, C$_1$-C$_3$ alkyl, C$_1$-C$_3$ alkoxy and halogen; A represents a C$_2$-C$_6$ carbon chain which may be saturated or unsaturated, and is optionally monosubstituted with C$_1$-C$_3$ alkyl, C$_1$-C$_3$ alkoxy, phenyl, CF$_3$, CH$_3$S, CN, halogen, OH, O, NO$_2$,

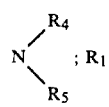

$$\overset{O}{\underset{\|}{OCH_2-C-OR_6,}} \overset{O}{\underset{\|}{R_6-C-O,}} \overset{O}{\underset{\|}{R_6-NH-C-O,}}$$

or is optionally disubstituted wherein one of the substituents is selected from the hereinabovenamed group and the second substituent is selected from C$_1$-C$_4$ alkyl or halogen; or A is a moiety represented by formula:

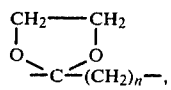

wherein n is an integer from 1 to 5; R is C$_1$-C$_4$ alkyl; R$_1$ is selected from hydrogen, CH$_3$ and CHO; R$_2$ is selected from hydrogen, C$_1$-C$_2$ alkyl, C$_3$ alkenyl or C$_3$ $_L$ alkynyl; R$_3$ is selected from C$_1$-C$_3$ alkyl, C$_3$ alkenyl or C$_3$ alkynyl, with the proviso that one of R$_1$ and R$_2$ must be hydrogen or CHO; R$_4$ and R$_5$ each are hydrogen or C$_1$-C$_3$ alkyl; R$_6$ is C$_1$-C$_3$ alkyl.

2. A compound according to claim 1, wherein X is O; Q is O; Y and Z each are selected from hydrogen, Cl, F, C$_1$-C$_4$ alkyl, C$_1$-C$_4$ alkoxy, NO$_2$; U is hydrogen; A is a saturated C$_2$-C$_4$ carbon chain optionally monosubstituted with C$_1$-C$_2$ alkyl, CH$_3$O, CH$_3$S, CH$_3$$_L$$_O$$_2$S, CN, Br, Cl, F, NHCHO and

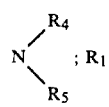

is hydrogen or CHO; R$_2$ and R$_3$ each are C$_1$-C$_2$ alkyl; R$_5$ each are hydrogen or C$_1$-C$_3$ alkyl.

3. A compound according to claim 1, wherein X is O; Q is O; Y is selected from hydrogen, CH$_3$ and Cl; Z is selected from hydrogen, CH$_3$, CH$_3$O, Cl and F; U is hydrogen; R$_1$ is hydrogen; R$_2$ and R$_3$ each are CH$_3$; A is selected from

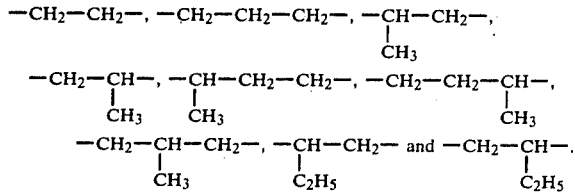

4. The compound according to claim 1, 1-methoxy-1-methyl-3-[3-(phenethyloxy)phenyl]urea.

5. The compound according to claim 1, 1-methoxy-1-methyl-3-[3-(4-methylphenethyloxy)phenyl]urea.

6. The compound according to claim 1, 1-methoxy-1-methyl-3-[3-(4-methoxyphenethyloxy)phenyl]urea.

7. The compound according to claim 1, 1-methoxy-1-methyl-3-[3-(3-methoxyphenethyloxy)phenyl]urea.

8. The compound according to claim 1, 1-methoxy-1-methyl-3-[3-(β-ethylphenethyloxy)phenyl]urea.

* * * * *

UNITED STATES PATENT AND TRADEMARK OFFICE
CERTIFICATE OF CORRECTION

PATENT NO. : 4,308,213

DATED : December 29, 1981

INVENTOR(S) : David M. Spatz

It is certified that error appears in the above-identified patent and that said Letters Patent is hereby corrected as shown below:

The cover sheet, column 1, Item No. 63, should read:

--- Continuation of Ser. No. 30,676, April 16, 1979, now abandoned.

Signed and Sealed this

Thirteenth Day of March 1984

[SEAL]

Attest:

Attesting Officer

GERALD J. MOSSINGHOFF

*Commissioner of Patents and Trademarks*

Dedication 4,308,213.—*David M. Spatz*, Trenton and *Barrington Cross*, Rocky Hill, N.J. META-(PHENYLALKOXY)PHENYL-N-METHOXY-N-METHYL-UREA COMPOUNDS. Patent dated Dec. 29, 1981. Dedication filed June 26, 1986, by the assignee, *American Cyanamid Co.*

Hereby dedicates to the Public the entire remaining term of said patent.
[*Official Gazette October 7, 1986.*]